(12) United States Patent
Sampas

(10) Patent No.: US 8,685,642 B2
(45) Date of Patent: Apr. 1, 2014

(54) ALLELE-SPECIFIC COPY NUMBER MEASUREMENT USING SINGLE NUCLEOTIDE POLYMORPHISM AND DNA ARRAYS

(75) Inventor: Nicholas Michael Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1496 days.

(21) Appl. No.: 11/881,932

(22) Filed: Jul. 30, 2007

(65) Prior Publication Data

US 2009/0035762 A1 Feb. 5, 2009

(51) Int. Cl.
*C12Q 1/68* (2006.01)
*C12N 15/00* (2006.01)
*C12N 15/11* (2006.01)

(52) U.S. Cl.
USPC ........................... 435/6; 435/320.1; 536/23.1

(58) Field of Classification Search
None
See application file for complete search history.

(56) References Cited

U.S. PATENT DOCUMENTS

| | | | |
|---|---|---|---|
| 5,925,525 A * | 7/1999 | Fodor et al. ................. | 506/3 |
| 6,110,709 A * | 8/2000 | Ausubel et al. .............. | 435/91.2 |
| 6,306,643 B1 | 10/2001 | Gentalen et al. | |
| 6,309,823 B1 | 10/2001 | Cronin et al. | |
| 6,368,799 B1 | 4/2002 | Chee | |
| 6,468,744 B1 | 10/2002 | Cronin et al. | |
| 6,582,909 B1 * | 6/2003 | Bougueleret et al. ......... | 435/6 |
| 6,852,490 B2 | 2/2005 | Gentalen et al. | |
| 6,892,007 B2 | 5/2005 | Chen | |
| 7,011,949 B2 | 3/2006 | Amorese et al. | |
| 7,097,976 B2 | 8/2006 | Kennedy | |
| 7,211,384 B2 | 5/2007 | Barrett et al. | |
| 2002/0042063 A1 * | 4/2002 | Kilian .......................... | 435/6 |
| 2006/0168679 A1 * | 7/2006 | Vanavichit et al. .......... | 800/278 |

FOREIGN PATENT DOCUMENTS

WO    WO 9511995 A1 *    5/1995

OTHER PUBLICATIONS

Killian (Proceedings of the International Congress, In the Wake of the Double Helix: From the Green Revolution to the Gene Revolution May 27-31, 2003, Bologna Italy, pp. 443-461).*
Wenzl et al (Proceedings the National Academy of Sciencies, USA (2004) vol. 101, pp. 9915-9920).*
G. Breen et al., "Short Technical Reports—Determining SNP Allele Frequencies in DNA Pools", Bio Techniques, vol. 28, No. 3, (2000), pp. 464-470.
Holland et al., "High-Throughput SNP Allele-Frequency Determination in Pooled DNA Samples by Kinetic PCR", Genome Research, (2000), pp. 258-266.
Esumi et al., "Restriction fragment length polymorphism of the rat albumin gene in Sprague-Dawley rats and its application in genetic study of analbuminemia", Nucleic Acids Research, vol. 10, No. 14 (1982) pp. 4247-4257.
Vos, et al., "AFLP: a new technique for DNA fingerprinting", Nucleic Acids Research, vol. 23, No. 21 (1995), pp. 4407-4414.
Bell et al., "Polymorphic DNA Region Adjacent to the 5' End of the Human Insulin Gene", PNAS—Proceedings of the National Academy of Sciences of the United States of America, vol. 78, No. 9, pp. 5759-5763, Sep. 1981.

* cited by examiner

*Primary Examiner* — Steven Pohnert

(57) ABSTRACT

Methods and systems for allelic detection and allele-specific copy number are provided herein. The described methods use identification of single nucleotide polymorphism using restriction enzymes and CGH analysis. Microarrays comprising probes designed by the described methods are provided. Also included are methods for identifying SNP sites and copy number in samples obtained from patient populations.

21 Claims, 2 Drawing Sheets

ALLELE-SPECIFIC COPY NUMBER MEASUREMENT USING SINGLE NUCLEOTIDE POLYMORPHISM AND DNA ARRAYS

BACKGROUND

Comparative genomic hybridization (CGH) and location analysis are important applications which allow scientists to make biological measurements involving genomics and study expression and regulation of genes in biological systems. Both CGH and location analysis entail quantifying or measuring changes in copy number of genomic sequences in biological or medical samples. Recently, cDNA microarrays and oligo microarrays have been used for CGH studies. An oligo-array based approach has several substantial advantages over other technologies, in that it allows the designer to position the probes anywhere within the genomic or polynucleotide sequence of interest and to select those sequences in such a way as to optimize their informativity and their performance. Oligo probes can be placed at any set of loci or positioned to span any genomic intervals of interest at whatever density is commensurate with the real-estate or area available on the microarray (in terms of number of features). The copy numbers of DNA over the genomic regions of interest can be evaluated by analyzing the hybridization of target sequences to the surface-bound probes. The oligonucleotide probe approach also offers the flexibility of focusing in on regions within exons or introns of expressed sequences, including pre-micro RNAs or intergenic regions and regulatory regions for location analysis, as well as any desirable admixture of the aforementioned.

Allele-specific copy number measurements are of increasing importance to the research community for the diagnosis of disease, especially in cytogenetics and cancer. Methods for the accurate detection of alleles and quantitation of their respective copy numbers allow the screening of many distinct candidate polymorphisms in the amount of time it would take to analyze a single polymorphism individually. Rapid assessment of single nucleotide polymorphisms (SNPs) using restriction fragment length polymorphism (RFLP) and allele-specific fluorophores have already been developed but typically require amplification through methods like PCR, and are not high throughput. Development of high throughput means for analyzing SNPs and allelic copy number would be beneficial.

SUMMARY

This disclosure relates to methods for allele-specific detection and genomic copy-number measurement. The methods described herein provide microarray platforms for the detection of single nucleotide polymorphisms (SNPs) using restriction enzyme analysis.

Methods for determining the presence of an allele comprising at least one SNP site in a DNA sample are provided. DNA samples are digested with at least one restriction enzyme, wherein the SNP site comprises a sequence that is cleaved by the restriction enzyme, a digested and an undigested and/or reference sample are hybridized to a microarray comprising a probe complementary to a sequence comprising the SNP site. The presence of the allele comprising the SNP site is determined by comparing the signal intensity of digested samples to an undigested and/or a reference sample, wherein a decrease in signal from the digested sample to the undigested and/or reference sample is indicative of the presence of the SNP and the allele. Allelic copy number and alterations in allelic copy number are also determined using the methods described herein.

The present disclosure describes a microarray platform for analysis of allele-specific copy number measurements and a method for designing a microarray platform for this analysis. The method for designing the array comprises selecting one or more restriction enzymes by identifying SNP sites for which the DNA with one of the allelic states of the SNP (either wild-type or variant) is cut by the restriction enzyme in a DNA sample and DNA with the other allelic state or states is not cut. Probes for the array are designed to comprise a sequence complementary to the SNP site and in some embodiments, the sequence complementary to the SNP site is located at about the center of the probe. Detecting sequences comprising the SNP site provides detection of an allele. Nucleic acid arrays or microarrays made by the methods are also provided herein.

DETAILED DESCRIPTION

Figure 1:
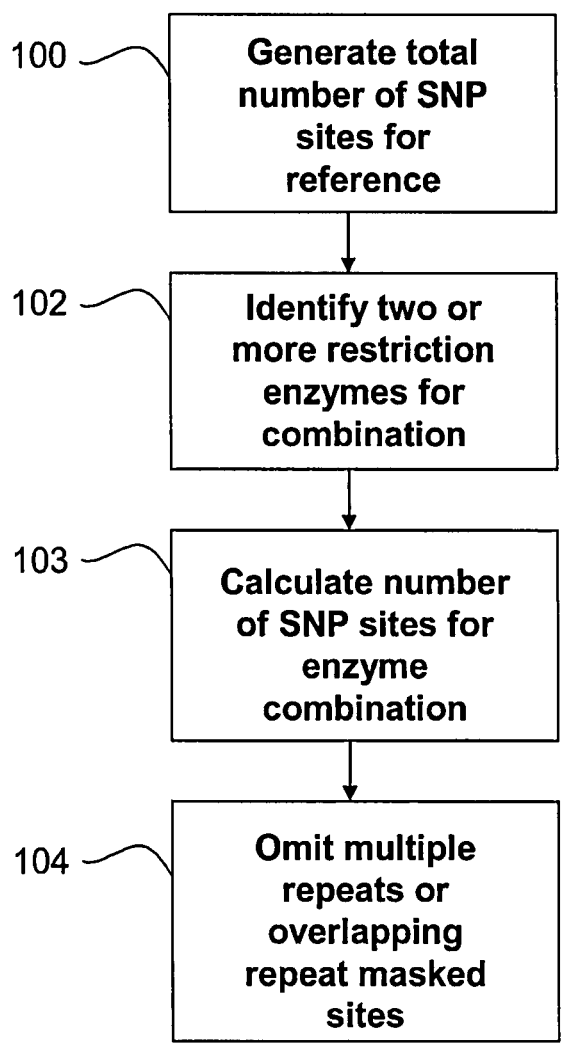
FIG. 1 is a flow chart showing a method for detection of an allele or allelic copy number.

Various embodiments of the present methods and systems will be described in detail with reference to the drawings, wherein like reference numerals represent like parts throughout the several views. Reference to various embodiments does not limit the scope of the claims attached hereto. Additionally, any examples set forth in this specification are not intended to be limiting and merely set forth some of the many possible embodiments for the claims.

Unless defined otherwise, all technical and scientific terms used herein have the same meaning as commonly understood by one of ordinary skill in the art. Although any methods, devices and material similar or equivalent to those described herein can be used in practice or testing, the methods, devices and materials are now described.

All publications and patent applications in this specification are indicative of the level of ordinary skill in the art and are incorporated herein by reference in their entireties.

In this specification and the appended claims, the singular forms "a," "an," and "the" include plural reference, unless the context clearly dictates otherwise. Unless defined otherwise, all technical and scientific terms used herein have the same meaning as commonly understood to one of ordinary skill in the art.

Definitions

The term "genome" refers to all nucleic acid sequences (coding and non-coding) and elements present in or originating from a single cell or each cell type in an organism. The term genome also applies to any naturally occurring or induced variation of these sequences that may be present in a mutant or disease variant of any virus or cell type. The term "reference assembly" refers to the published or private genomic sequence of an organism, typically known by the species or subspecies *used* to define the probes and genomic sequences. The reference assembly may have sequences consistent with either the common allele or minor alleles for any single nucleotide polymorphism. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism For example, the reference assembly of the human genome includes approximately $3 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of X chromosomes (female) for a total of 46 chromosomes. A genome of a cancer cell may contain variable numbers of each chromosome, in the form of deletions, rearrangements and amplification of any subchromosomal region or DNA sequence.

The terms "nucleic acid" and "polynucleotide" are used interchangeably herein to describe a polymer of any length, e.g., greater than about 10 bases, greater than about 100 bases, greater than about 500 bases, greater than about 1000 bases, usually up to about 10,000 or more bases composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length. Oligonucleotides are usually synthetic and, in many embodiments, are under 50 nucleotides in length.

The term "oligomer" is used herein to indicate a chemical entity that contains a plurality of nucleotide monomers, i.e., a nucleotide multimer. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other nucleic acids that are C-glycosides of a purine or pyrimidine base, polypeptides (proteins), polysaccharides (starches, or polysugars), and other chemical entities that contain repeating units of like chemical structure.

The term "sample" as used herein relates to a material or mixture of materials, typically, although not necessarily, in fluid form, containing one or more components of interest. Samples include, but are not limited to, biological samples obtained from natural biological sources, such as cells or tissue. The samples may also be derived from tissue biopsies and other clinical procedures.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "surface-bound polynucleotide" refers to a polynucleotide that is immobilized on a surface of a solid substrate, where the substrate can have a variety of configurations, e.g., a sheet, bead, or other structure. In certain embodiments, the collections of oligonucleotide probe elements employed herein are present on a surface of the same planar support, e.g., in the form of an array.

The phrase "labeled population of nucleic acids" refers to mixture of nucleic acids that are detectably labeled, e.g., fluorescently labeled, such that the presence of the nucleic acids can be detected by assessing the presence of the label. A labeled population of nucleic acids is "made from" a chromosome sample, the chromosome sample is usually employed as template for making the population of nucleic acids.

A "biological model system," or "model system," as provided herein, refers to a system for which a quantitative response in a microarray system can be expected with certainty. Exemplary model systems include, without limitation, titration series with different RNA samples at different concentrations, samples with known genomic aberrations, samples to be used for comparative genomic hybridization experiments, etc. The biological model systems are used to perform microarray experiments, to validate probes designed for microarray applications, to obtain sets of training data for statistical analysis, etc.

The term "array" encompasses the term "microarray" and refers to an ordered array presented for binding to nucleic acids and the like.

An "array," includes any two-dimensional or substantially two-dimensional (as well as a three-dimensional) arrangement of spatially addressable regions bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

In those embodiments where an array includes two more features immobilized on the same surface of a solid support, the array may be referred to as addressable. An array is "addressable" when it has multiple regions of different moieties (e.g., different oligonucleotide sequences) such that a region (i.e., a "feature" or "spot" of the array) at a particular predetermined location (i.e., an "address") on the array will detect a particular sequence. Array features are typically, but need not be, separated by intervening spaces. In the case of an array in the context of the present application, the "population of labeled nucleic acids" will be referenced as a moiety in a mobile phase (typically fluid), to be detected by "surface-bound polynucleotides" which are bound to the substrate at the various regions. These phrases are synonymous with the arbitrary terms "target" and "probe", or "probe" and "target", respectively, as they are used in other publications.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there are intervening areas that lack features of interest.

The term "substrate" as used herein refers to a surface upon which marker molecules or probes, e.g., an array, may be adhered. Glass slides are the most common substrate for biochips, although fused silica, silicon, plastic, flexible web and other materials are also suitable.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably. The terms "hybridizing," "hybridizing specifically to," and "specific hybridization" as used herein, refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term "stringent assay conditions" refers to the combination of hybridization and wash conditions.

A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions determines whether a nucleic acid is specifically hybridized to a probe. Wash conditions used to identify nucleic acids may include, e.g.: a salt concentration of about 0.02 M at pH 7 and a temperature of about 20° C. to about 40° C.; or, a salt concentration of about 0.15 M NaCl at 72° C. for about 15 minutes; or, a salt concentration of about 0.2×SSC at a temperature of about 30° C. to about 50° C. for about 2 to about 20 minutes; or, the hybridization complex is washed twice with a solution with a salt concentration of about 2×SSC containing 1% SDS at room temperature for 15 minutes and then washed twice by 0.1×SSC containing 0.1% SDS at 37° C. for 15 minutes; or, equivalent conditions. Stringent conditions for washing can also be, e.g., 0.2×SSC/0.1% SDS at 42° C. See Sambrook, Ausubel, or Tijssen (cited below) for detailed descriptions of equivalent hybridization and wash conditions and for reagents and buffers, e.g., SSC buffers and equivalent reagents and conditions.

A specific example of stringent assay conditions is rotating hybridization at 65° C. in a salt based hybridization buffer with a total monovalent cation concentration of 1.5M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA, or the like.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not especially distinct. In other words, a mixture is not addressable. To be specific, an array of surface-bound polynucleotides, as is commonly known in the art and described below, is not a mixture of capture agents because the species of surface-bound polynucleotides are spatially distinct and the array is addressable.

"Isolated" or "purified" generally refers to isolation of a substance (compound, polynucleotide, protein, polypeptide, polypeptide, chromosome, etc.) such that the substance comprises the majority percent of the sample in which it resides. Typically in a sample a substantially purified component comprises 50%, preferably 80%-85%, more preferably 90-95% of the sample. Techniques for purifying polynucleotides, polypeptides and intact chromosomes of interest are well known in the art and include, for example, ion-exchange chromatography, affinity chromatography, sorting, and sedimentation according to density.

The terms "determining" and "evaluating" are used interchangeably to refer to any form of measurement, and include determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

If a surface-bound polynucleotide "corresponds to" a chromosome, the polynucleotide usually contains a sequence of nucleic acids that is unique to that chromosome. Accordingly, a surface-bound polynucleotide that corresponds to a particular chromosome usually specifically hybridizes to a labeled nucleic acid made from that chromosome, relative to labeled nucleic acids made from other chromosomes. Array features, because they usually contain surface-bound polynucleotides, can also correspond to a chromosome.

A "non-cellular chromosome composition", as will be discussed in greater detail below, is a composition of chromosomes synthesized by mixing predetermined amounts of individual chromosomes. These synthetic compositions can include selected concentrations and ratios of chromosomes that do not naturally occur in a cell, including any cell grown in tissue culture. Non-cellular chromosome compositions may contain more than an entire complement of chromosomes from a cell, and, as such, may include extra copies of one or more chromosomes from that cell. Non-cellular chromosome compositions may also contain less than the entire complement of chromosomes from a cell.

An "allele" refers to any of two or more alternative forms of a gene that occupy the same locus on a chromosome. If two alleles within a diploid individual are identical by descent (that is, both alleles are direct descendants of a single allele in an ancestor), such alleles are called autozygous. If the alleles are not identical by descent, they are called allozygous. If two copies of same allele is present in an individual, the individual is homozygous for that gene. If different alleles are present in an individual, the individual is heterozygous for that gene.

The term "single nucleotide polymorphism" refers to a polymorphism where each allele differs by the replacement of a single nucleotide in the DNA sequence of the allelic gene. In some cases, the single nucleotide change can alter the structure and function of the corresponding gene product (i.e. protein). The term is commonly abbreviated as "SNP" and the terms "single nucleotide polymorphism" and "SNP" are used interchangeably herein. For most SNPs, only two of the four possible nucleotides (A, T, C, or G) are observed. SNPs can be bi-, tri-, or tetra-allelic polymorphisms. However, in humans, tri-allelic and tetra-allelic SNPs are rare, and SNPs are simply referred to as bi-allelic markers.

A "restriction enzyme" is a protein that recognizes specific, short nucleotide sequences in a DNA sequence and cleaves the DNA at those sites. The short nucleotide sequences are termed recognition sites or sequences that are typically 4, 5, 6, or 8 bases long. Restriction enzymes are identified as 4-base cutters, 6-base cutters, etc.

A "probe" means a polynucleotide that can specifically hybridize to a target nucleotide, either in solution or as a surface-bound polynucleotide.

The term "validated probe" means a probe that has been passed by at least one screening or filtering process in which experimental data related to the performance of the probes was used a part of the selection criteria.

"In silico" means those parameters that can be determined without the need to perform any experiments, by using information either calculated de novo or available from public or private databases.

The term "duplex $T_m$" refers to the melting temperature of two oligonucleotides that have formed a duplex structure. Duplex $T_m$ is calculated by a simple formula where each matching GC pair gets a value of 2, and each matching AT pair gets a value of 1. The sum of these approximate values gives the melting temperature.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention without following the example embodiments and applications illustrated and described herein, and without departing from the true spirit and scope of the present invention, which is set forth in the following claims.

Methods for Determining the Presence of an Allele and Allele Copy Number

One aspect of the disclosure provides a method for determining if an allele comprising at least one SNP site is present in a DNA sample. The method comprises: digesting one or more DNA samples with at least one first restriction enzyme, wherein a DNA sample comprises at least one SNP site that comprises a sequence cleaved by the least one first restriction enzyme; labeling the sample with one or more detectable labels and labeling an undigested DNA sample such that each sample is distinguishable from other samples; hybridizing the samples to a microarray comprising a probe complementary to a sequence comprising the at least one SNP site, wherein the at least one of the SNP site comprises a sequence cleaved by the at least one first restriction enzyme; and determining if the allele comprising the at least one SNP site cleaved by the at least one first restriction enzyme is present in the sample by comparing the signal from digested sample to the signal from the undigested samples, wherein a change in the signal from the digested sample as compared to the undigested sample indicates the presence of the at least one SNP site and the presence of the at least one SNP site is indicative of the presence of the allele. In some embodiments, the signal from the digested sample is decreased as compared to the undigested sample. In some embodiments, no decrease in the signal between digested and undigested samples is indicative that an allele comprising the SNP site is not present in the sample.

In some embodiments, a set of single nucleotide polymorphism (SNP) sites in a human genome reference assembly is determined. A set of SNPs can be determined by analyzing publicly available sequence information for genes and identifying alternative forms of a gene having a nucleotide change. Some databases such as Genecards, for example, provide sequences of SNPs. The SNP sites are analyzed for the presence of a restriction enzyme cleavage sequence. In some embodiments, a set of SNP sites identified by a cleavage sequence for a specific enzyme can be further reduced by eliminating SNP sites that are cut by multiple enzymes. In some embodiments, a set of SNP sites identified by a cleavage sequence for a specific enzyme can be further reduced by eliminating SNP sites that overlap repeat mask regions of the genome.

Previously designed probe methods intentionally avoid probe sequences within the reference assembly that contain restriction enzyme cleavage sites for enzymes used in the assay to decrease the computational power needed to identify optimal probes (see, e.g., U.S. Patent Pub. No. 2006/0110744, incorporated herein by reference). Nevertheless, microarrays with hundreds of thousands of probes may typically include hundreds of sites where SNPs alter the target sequence from the reference assembly such that the altered targets may contain restriction sites within DNA of a subset of samples from different individuals (at sites where SNPs are present with respect to the reference assembly). Of these SNPs, some are sufficiently well centered within the probe that they are destabilizing with respect to the hybrid formed between SNP-containing target sequences and probes derived from the reference assembly. These SNP sites, however, may not be detected if probes are designed to avoid probe sequences that avoid restriction sites and even if not so designed, it may be unclear whether an allele for a specific gene is being detected or whether there is some other reason for the change in signal intensity.

Figure 2:
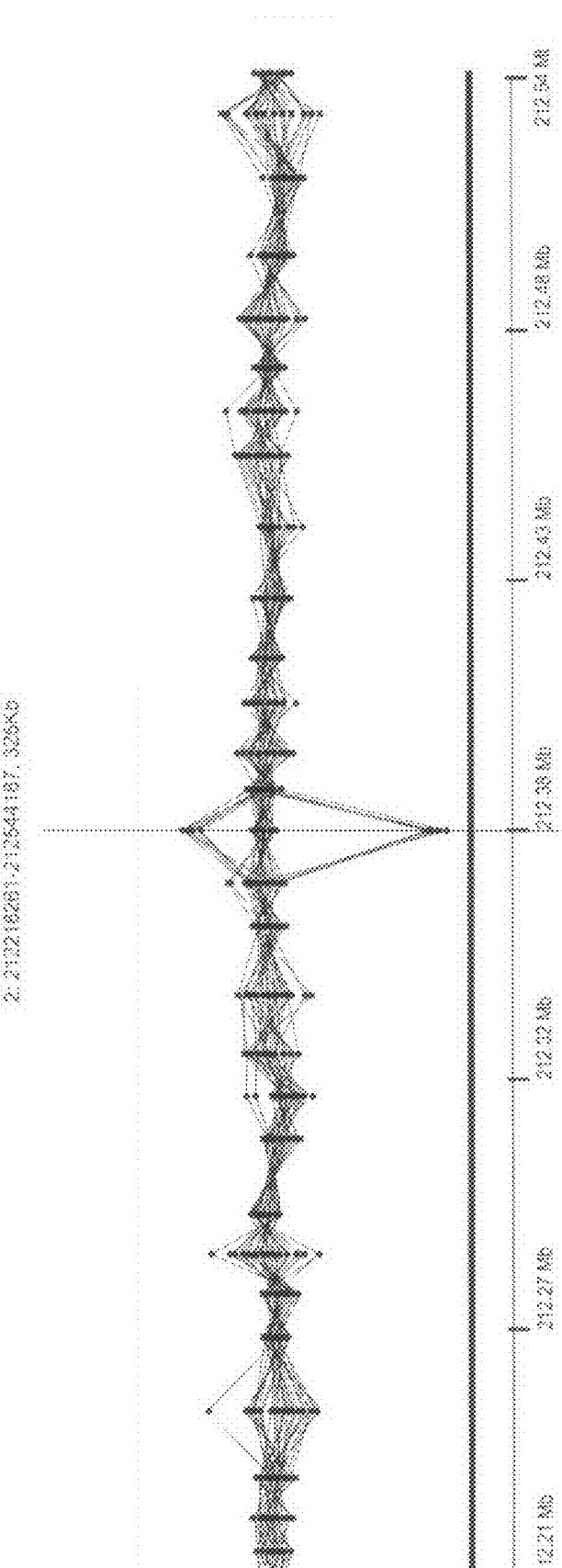
FIG. 2 shows three different signal levels (Log Ratios) for SNP sites in samples from a number of different individuals for the ErbB4 gene. Both the heterozygous and homozygous mutant and wild type are demonstrated. The drop put in signal is expected to be associated with the homozygous allelic state where the target is cut by the enzyme.

One such example shown in FIG. 2, at least one site detected by a single probe showed differential copy number measurements between samples in the ErbB4 gene. Different samples from multiple individuals show a distribution for a given probe, with three distinct clusters of LogRatio values. The lower signals for one cluster of samples indicates that both copies of the DNA (one for each chromosome) were cut homozygously relative to the reference sample for which there were two intact copies of the allele present in the sample. Another cluster demonstrates that only the copy of the DNA on one chromosome in each sample is cut by the enzyme while the other copy was intact (i.e. heterozygously; a single copy of the allele present in the sample), and a third cluster indicates a third set of samples for which neither target molecule on either chromosomes is cleaved.

The methods described herein involve the use of one or more restriction enzymes that allow for the detection of many SNPs, and therefore, many different alleles. There are approximately 10 million known SNPs in the human genome, and a 4-base cutter will cut a random sequence at a frequency of about 1 site per 256 bases within the target sequence. A SNP in any one of the four bases of the site will change the nature of the polymorphic site from a cutting to a non-cutting site and vice-versa. Therefore, a 4-base cutter enzyme produces approximately 150,000 cleavage sites (although the actual number of sites will vary with the enzyme used). The number of cleavage sites increases with each additional enzyme with a different cut sequence. Therefore, the present methods can be used to detect SNPs on the scale of hundreds of thousands.

Accordingly, the present disclosure provides methods for determining if an allele comprising at least one SNP site is present in a DNA sample. In an embodiment, the DNA samples analyzed by the methods of the invention include genomic DNA samples from an organism. In another embodiment, the DNA sample includes DNA prepared from total RNA isolated from tissues or cells collected from a subject such as patient or from a patient population. In an aspect, the genomic DNA sample is from a single chromosome, isolated for example by flow sorting. In some embodiments, DNA samples from several individuals are pooled. In other embodiments, a DNA sample obtained from an individual is analyzed and compared to one or more other individuals. In some embodiments, the DNA samples may be obtained from an individual or individuals having a particular phenotype, for example, a particular disease or disorder.

The DNA sample can be pretreated in order to reduce the size of the DNA fragments. In some embodiments the DNA sample is pretreated with a predigestion restriction enzyme and/or may be sheared using mechanical means, including sonication. In some embodiments, the DNA sample comprises DNA fragments of about 100 to 20,000 base pairs, or about 500 to 10,000 base pairs. Such methods are known to those of skill in the art.

In an embodiment, a DNA sample (whether pretreated or not) comprising at least one SNP site is digested with at least one restriction enzyme, wherein the restriction enzyme cleaves the DNA sample at the at least one SNP site as shown in operation 100 of FIG. 1. In some embodiments, the DNA sample is labeled before digestion. If more than one DNA sample is used, then each sample is digested with a different restriction enzyme. In an embodiment, a numerical analysis of the cleavage sites that are present in a genomic reference assembly can be determined using a database containing approximately 10,000,0000 SNPs. Such databases are publicly accessible for the human genome. This analysis provides at least one or more or a set of restriction enzymes that can be used for SNP identification according to the methods described herein.

In some embodiments, a restriction enzyme or a set of restriction enzymes are selected that allow for the identification of the maximum number of alleles present in a sample or in the least, in a target sequence. An analysis of the frequency of the SNPs in the population from which the samples are drawn provides for identification of a restriction enzyme or set of restriction enzyme that provides for detection of a number of different alleles, of detection of a specific allele such as may be associated with a particular phenotype, disease, or disorder, and/or detection of the allele copy number. In some embodiments, one or more restriction enzymes may be selected that cut at SNP sites that are located in the middle of a probe sequence used for detecting the target sequence. In some embodiments restriction enzymes can be analyzed for cutting efficiency, and the number of cleavage sites within SNP sites. In some embodiments, a restriction enzyme is selected that allows for detection of at least one SNP site in an allele. Restriction enzymes and the sequences at which they cleave are known and are publicly accessible.

In some embodiments, one or more restriction enzyme selected for use with the present methods may be 4-base cutters. That is, the restriction enzyme is capable of cutting a nucleotide sequence at intervals of 4 bases. In aspects, the 4-base cutter enzymes maybe enzyme such as, without limitation, RsaI or AluI, for example. In other embodiments, the enzymes selected for the current methods may be 5- or 6-base cutters (i.e. the enzyme cuts a sequence at intervals of 5 bases or 6 bases). Combinations of 4-, 5- and 6-base cutter enzymes are also possible. In other embodiments, a combination of multiple restriction enzymes can be used in place of just two restriction enzymes. More complex mixtures of enzymes may be used, expanding the number of SNP-sites available, and making the microarray platform incorporating the expanded number of SNP a more powerful assay tool for CGH and allele-specific copy number detection.

The digested sample or samples are then labeled with a detectable label (i.e. a chromogenic moiety or a fluorophore) such that each sample is labeled with a different label and can be distinguished from other samples as shown in operation 102 of FIG. 1. The digested DNA sample may be labeled if not labeled previously. An undigested DNA sample is labeled with a different label. In some, embodiments, one or more reference samples are labeled, each with a different label.

The labeled samples are then hybridized to a microarray comprising a probe or probes complementary to sequences comprising SNP sites present in the DNA sample or samples as shown in operation 102 in FIG. 1. The signal from the labeled digested sample to the signal from labeled undigested sample is compared as shown in operation 103 of Figure. A change in signal intensity when the labeled digested sample is compared to the labeled undigested sample is indicative of the presence of the SNP site which is indicative of the presence of the allele. If an allele comprising at least one SNP site cleavable by a first restriction enzyme is present in the DNA sample or samples, the signal from the sample or samples digested with at least one restriction enzyme will be decreased relative to other samples, such as for example, any undigested samples or samples digested with a different restriction enzyme. The presence or absence of at least one SNP site in the sample is determined and provides identification of the presence or absence of the allele. In some embodiments, no decrease in the signal between digested and undigested samples is indicative that an allele comprising the SNP site is not present in the sample.

In an embodiment, the methods described herein can further employ a reference sample on the microarray. In some embodiments, the reference sample is a sample comprising one or more known allele and/or copy number of the allele and comprises a nucleotide sequence comprising the at least one SNP site that can be cleaved by a first restriction enzyme. In some embodiments, the reference sample is not subjected to digestion by the first restriction enzyme, and optionally may be digested with a different restriction enzyme. The reference sample is labeled and then hybridized to the microarray along with the other labeled digested and/or undigested DNA samples. The signal from the digested and/or undigested sample signal is compared to the reference sample to determine the presence or absence of the allele, the allelic copy number, and any changes in copy number of the samples relative to the reference sample as sown in operation 104 of FIG. 1. If the signal for the particular sequence comprising the SNP site is decreased in the digested sample as compared to undigested and/or reference samples, the allele that comprises the SNP site is present in the sample. To determine the allele copy number the intensity of the signal of the undigested sample is compared to the reference sample having a known allelic copy number.

In an embodiment of the present methods, the one or more DNA samples are split to provide first and second sub-samples for each DNA sample. The first sub-sample is labeled with a first detectable label and the second sub-sample is labeled with a second detectable label. The first sub-sample is then digested with at least a second restriction enzyme (i.e. an enzyme that cleaves the DNA sample at a different SNP site than the first restriction enzyme) to produce a double-digested sample. The second sub-sample is left undigested by the second restriction enzyme. The method further comprises determining if the second SNP site cleaved by the second restriction enzyme is present in the samples by comparing the signal from the second sample to the signal from undigested sample and/or the first sample, wherein a decrease in the signal from the second sample indicates presence of the second SNP site and wherein the presence of the second SNP site is indicative of presence of a second allele.

In other embodiments, the DNA sample is split into at least three sub-samples, with each sub-sample digested with a different restriction enzyme, and leaving one sub-sample undigested.

Two or more samples or sub-samples, whether digested or undigested, are differentially labeled to be easily distinguishable from one another. In an aspect, a first sample or sub-sample is labeled with a first detectable label and a second sample or sub-sample with a second detectable label. Each of the detectable labels comprises a fluorophore, such as Cy3 or Cy5, or a chromogenic moiety or dye, such as an Alexa dye, for example.

Methods as described herein comprise hybridizing the samples to a microarray comprising a probe complementary to a sequence comprising the at least one SNP site, wherein the at least one of the SNP site comprises a sequence cleaved by the at least one first restriction enzyme. In some embodiments, for each SNP site, two probes are typically used: one comprising the wild-type sequence at the SNP site and the other comprising the sequence of the SNP site. In some embodiments, the array may also comprise a probe comprising, for example, a base deletion at the SNP site, or the substitution of a generic base at the SNP site. In this case the difference of the signals produced by the perfectly matching sequences and the mismatching sequences are equalized to some extent, making the difference in signal due to the digested sequences and undigested sequences more readily distinguishable from the differences due to mismatches between the target and the probe. In some embodiments, the probe is designed to include a sequence complementary to the SNP site away from either end of the probe. In some embodiments, the sequence complementary to the SNP site is located within about 10 nucleotides of the center of the probe. In an embodiment, the probe has 30 to 60 nucleotides and the sequence complementary to the SNP site is located between nucleotides 10 to 15 or nucleotides 30 to 40 of the probe.

In embodiments, the present methods also provides for the CGH analyses of samples. For probes where the target sequences are not cut by the enzyme copy-number information is attained for the uncut allele. Additionally, probes not specific to SNPs or restriction sites may be utilized on the same array to yield supplementary copy-number information or to provide other genetic marker information. For example, a probe that detects a specific allele of an HLA (human leukocyte antigen marker, also know as a histocompatibility marker) may be included in the array. Such methods would allow the establishment of a relationship between the presence of specific alleles and that HLA marker. In this way any subset of probes on the array may be for the purpose of measuring allele-specific copy number information, whereas another subset is for the purpose of deriving non-allele-specific copy number information.

The assay can also be made more sensitive and powerful by the use of an array of arrays located on a single slide or array substrate. In an array of arrays (such as 8-pack of 12-pack arrays), each array could have a different set of probes specific to cleavage sites created by different sets or combinations of enzymes. For combinations of two 4-base cutter enzymes, approximately 300,000 potentially viable SNP-related cleavage sites are likely to be identified. Exemplary 4-base cutters include restriction enzymes such as RsaI and AluI. Identification of cleavage sites in a genomic DNA sample for an RsaI/AluI combination were performed and yielded an estimated 435,000 SNPs.

The assay may use one or more enzymes, a two-color hybridization or a multicolor hybridization reaction to improve performance. For example, the assay may be improved using multiple restriction enzyme combinations, where the sample is split into different aliquots, and each aliquot is digested with a different enzyme or combination of enzymes, with each aliquot labeled differently than other aliquots. Differently labeled samples can then be hybridized to a number of arrays, or the samples can be recombined and hybridized to a single array, with the signal intensities read by a multi-color readout.

In an embodiment, labeled DNA samples are hybridized to one array, and reference samples are hybridized to another array. Allele-specific measurements are made by measuring the signal in a first channel with an enzyme that cuts at a specific site and by comparing the signal from that channel to the signal from the same sample cut with a different enzyme in a second channel. If a reference sample with known SNP state is labeled and hybridized in a different channel, measurements can be made not only with respect to allele-specificity but also copy number changes relative to the reference sample.

In some embodiments of the methods described herein, genomic DNA samples obtained from a plurality of different subjects or patients are pooled to form a single DNA sample for allelic measurements. In an aspect, the DNA samples are obtained from a subject of subjects with a disease or disorder and comprise a genetic marker for the disease or disorder. In another aspect, each of the plurality of samples obtained from the subject or subjects comprise an additional genetic marker that is the same in each sample. In an aspect, the genetic marker associated with the subject's disease or disorder comprises a set of known SNP sites, where the SNP sites are selected due to a known relationship between the subject's disease state or phenotype and the SNP site.

The methods described herein provide the ability to perform allele-specific copy number measurements, wherein the relative abundance of each allele is measured. The ability to measure allele-specific copy number may be limited by the completeness of the reaction with each restriction enzyme or combination of enzymes, and may also be affected by cross-hybridization of targets cut by the enzymes to the probe. Other factors to consider with the present methods include the frequency of SNPs in the target region or population of interest, in silico considerations, and the discrimination between cut and uncut target sequences.

Microarray Platform Design and Nucleic Acid Arrays

The present description provides novel methods and systems for designing a microarray platform useful for detection of single nucleotide polymorphisms (SNPs) and for determining allele-specific copy number changes in a genomic region of interest. General methods that utilize probe/target hybridization experiments and/or unique data analysis techniques to identify and select nucleotide probe(s) for microarray applications were described in U.S. Patent Publication No. 2006/0110744. The methods described herein provide methods for identifying single nucleotide polymorphisms (SNPs) using restriction enzymes known to cut a target nucleotide sequence at particular SNP sites on one or more alleles. The pattern of SNP sites on the alleles are then used to determine allele-specific copy number changes.

The methods provided herein are particularly useful with comparative genome hybridization (CGH) microarrays, such as microarrays based on the human or mouse genome. These methods permit more cost-effective and efficient identification of gene regions or sections which can be associated with human disease, points of therapeutic intervention, and potential toxic side-effects of proposed therapeutic entities. Specifically, the methods described herein can be used in conjunction with CGH assays to detect allele-specific copy number alterations.

The present description provides methods, systems and computer readable media for identifying and selecting nucleic acid probes for detecting a target with a nucleic acid probe array or microarray. The methods comprise: the selection of genomic nucleotide ranges of interest or nucleotide sequences of interest, determining appropriate target sequences for SNP analysis, analyzing target sequences for specific properties such as the number of cuts made by a particular restriction enzyme, and reducing the number of probes to a value appropriate for placement on a microarray.

In one aspect, the disclosure provides a method for designing a microarray platform for analysis of allele detection, comprising: selecting one or more restriction enzymes by identifying a set of potential single nucleotide polymorphism (SNP) sites in a genome reference assembly that are cut by the one or more restriction enzymes; omitting any multiple restriction sites cut by the one or more enzymes, or omitting sites that overlap with repeat masked regions of the genome to obtain a reduced set of SNP sites; and designing a microarray platform incorporating one or more probes to detect each of the reduced set of SNP sites, wherein the probes are complementary to a sequence comprising a SNP site that is cut by the one or more restriction enzymes, wherein detecting the sequence comprising the SNP site provides detection of an allele. In some embodiments, a restriction enzyme is selected based upon the efficiency of cutting. Efficiency of cutting by a restriction enzyme can readily be determined by analyzing a reference sample.

In designing an array comprising high-performance probes that comprehensively covers a whole genome (e.g. the human genome) the entire genomic sequence is searched when generating specific candidate probes. This homology search is potentially the most time-consuming part of the probe design process. Ideally, a homology search would be the first part of the process, however because of the scale of the human genome executing an exhaustive search of all possible short oligo probes (<100 bases), can take computation time on the scale of a CPU year (based on ProbeSpec), for modern 3 GHz processors. This computation time can be reduced by any of a number of methods, most involving reducing the scale of the search. For example, known highly repetitive sequences can be removed by a process called RepeatMasking. Repeat-masked genomic sequences are publicly available on the web (e.g. UCSC's www.genomebrowser.org). Another approach is to reduce the number of probe sequences being searched up-front. This can be done on the basis of any known property of the probe, from thermodynamic properties, such as duplex-Tm and hairpin free energy, to position on the genome. The present description provides methods which apply known probe information as a screening process to reduce the number of probe sequences to be analyzed in a homology search, thus reducing the computation time needed to identify appropriate probes for a CGH based array.

In an aspect, a method of reducing the number of target sequences is performed by analyzing sequences with known SNPs for nucleotide sequences that are cut by a single restriction enzyme, or are cut by a first restriction enzyme but not cut by a second restriction enzyme. Sequences of a gene comprising SNP sites are known to those of skill in the art and are accessible in publicly available databases. An analysis of the frequency of the SNPs in the population from which the samples are drawn provides for identification of a restriction enzyme or set of restriction enzyme that provides for detection of a number of different alleles, of detection of a specific allele such as may be associated with a particular phenotype, disease, or disorder, and/or detection of the allele copy number.

This analysis may generate a large number of SNP sites especially in the case of a genomic analysis. Restriction enzymes may be selected to reduce the number of SNP sites that are cleaved in the sample. Today, typical arrays can include about 250,000 different probes, which would allow for detection of a comparable number of different SNP sites. In the case, where it is desired to detect higher number of SNPs multiple arrays can be utilized or higher density arrays may be utilized. In some embodiments, a restriction enzyme is selected to avoid cleavage at the same or overlapping site by different restriction enzymes. In addition, target sequences can be reduced by excluding those sequences that overlap with repeat masked regions of the genome. In some embodiments, one or more restriction enzymes may be selected that cut at sites that are located in the middle of a probe sequence used for detecting the target sequence. In some embodiments restriction enzymes can be analyzed for cutting efficiency, and the number of cleavage sites within SNP sites that they effectively produce. In some embodiments, a restriction enzyme is selected that allows for detection of at least one SNP site in an allele. One or more of the selection criteria may be utilized to provide a reduced number of SNP sites. Alternatively the target sequence can be selected to generate a smaller number of SNP sites. Restriction enzymes and the sequences at which they cleave are known and are publicly accessible.

One or more restriction enzymes may be employed in the methods described herein. Restriction enzymes may cut at a 4-nucleotide sequence, a 5-nucleotide sequence, or a 6-nucleotide sequence, for example. Combinations of restriction enzymes that cut at nucleotide sequences of different lengths can be used. The nucleotide sequences cleaved by a particular restriction enzyme are known to those of skill in the art.

Designing a microarray involves determining the amount of "real estate" (number of probes) that is available for the final array. The array designer also determines the amount of probes or "real estate" to use for specified regulatory regions, intergenic regions as well the amount of probes necessary to adequately cover introns and exons of the chromosomes of interest. Initially, a designer may generate 20 million or more candidate probes and need to filter the probes for certain probe properties or parameters to obtain a final array with a number of probes commensurate with an assay cost and information content necessary to the experiment or diagnostic of interest. Intermediate arrays are manufactured in some embodiments of the methods of the invention, which have a redundancy of 3 fold or more over the number of probes selected for the final array, these intermediate arrays are utilized to screen candidate probes for certain probe properties by direct or indirect experimentation.

In many embodiments, the oligonucleotides (i.e. probes) contained in the features of this disclosure have been designed according to one or more particular parameters to be suitable for use in a given application, where representative parameters include, but are not limited to: length, melting temperature ($T_m$), non-homology with other regions of the genome, secondary structure, hybridization signal intensities, kinetic properties under hybridization conditions, etc., see e.g., U.S. Pat. No. 6,251,588, the disclosure of which is herein incorporated by reference.

In an aspect, at least one probe can be designed that has a sequence complementary to the sequence of a gene or target sequence comprising a SNP, wherein the SNP is cut by a restriction enzyme, or cut by a first restriction enzyme but not cut by a second restriction enzyme. Such target sequences can be identified by analyzing sequences comprising SNPs for sequences that are cut by the first restriction enzymes. In some embodiments, for each SNP site, two probes are typically used: one comprising the wild-type sequence at the SNP site and the other comprising the sequence of the SNP site. In some embodiments, the array may also comprise a probe comprising, for example, a base deletion at the SNP site, or the substitution of a generic base at the SNP site. In this case the difference of the signals produced by the perfectly matching sequences and the mismatching sequences are equalized to some extent, making the difference in signal due to the digested sequences and undigested sequences more readily distinguishable from the differences due to mismatches between the target and the probe.

In some other aspects, probes can also be designed to detect a sequence of a gene comprising at least one SNP using duplex $T_m$ matching as a design method. In these design methods, candidate probes, with sequences complementary to a target region of interest are identified, and the sequence of the entire target region is searched to find all sequences that can form stable hybrids with the candidate probes (i.e. sequences with homology to the candidate probes). The most homologous sequences are selected, and the candidate probes are modified by deletion or substitution of one or more nucleotides in the candidate probe sequence. The deletion or substitution destabilizes the hybrid pair formed between the candidate probe and the undesired sequences by reducing the $T_m$ for the hybrid pairs, below the computed $T_m$ of the hybrid between the probe and the desired target sequence. Candidate probes are selected such that (a) the hybrid between the destabilized probe and the desired target is not melted at the chosen assay temperature, and (b) the hybrids between the probe and all undesired homologous targets are melted at the chosen assay temperature, and (c) the melting temperatures of the desired and undesired hybrids are as different as possible. In an aspect, the probes have a $T_m$ difference of about 0.5° C. to about 4° C. when compared to a perfectly matched probe.

In yet other aspects, probes can be designed with a generic base at the SNP site. A generic base is a nucleotide analog that binds two or more distinct bases with similar binding affinity, and can therefore be used to replace the two or more distinct bases. Probes can also be designed with a deletion at the SNP site. These probes are distinguishable from deletion probes where specific bases have been deleted, or the sequence has been truncated, but the deletion does not occur at a SNP site.

In yet other aspects, the probe is designed to include a sequence complementary to the SNP site away from either end of the probe. In some embodiments, the sequence complementary to the SNP site is located within about 10 nucleotides of the center of the probe. In other embodiments, the sequence complementary to the SNP site is located within about 10 nucleotides of an end of the probe. In an embodiment, the probe has 30 to 60 nucleotides and the sequence complementary to the SNP site is located between nucleotides 10 to 15 or nucleotides 30 to 40 of the probe.

In an aspect, designed probes are amplified using standard techniques such as ligation and thermocycling, polymerase chain reaction, and other methods known to those of skill in the art for amplifying nucleotide sequences. In other aspects, probes designed for use in CGH applications are amplified enzymatically. Enzymatic amplification uses highly processive DNA polymerases, such as Phi29, for example, which synthesize DNA sequences by multiple strand displacement (MDA). This method can generate thousands of high molecular weight copies of genomic DNA without using ligation or thermocycling. Highly processive enzymes can be used to amplify DNA samples from tissue biopsies, and DNA from highly purified cell populations obtained using methods such as laser capture microdissection (LCM) or flow cytometry.

Standard hybridization techniques (using high stringency hybridization conditions) are used to probe subject array. Suitable methods are described in references describing CGH techniques (Kallioniemi et al., *Science* 258: 818-821 (1992) and WO 93/18186). Several guides to general techniques are available, e.g., Tijssen, *Hybridization with Nucleic Acid Probes, Parts I and II* (Elsevier, Amsterdam 1993). For a descriptions of techniques suitable for in situ hybridizations see, Gall et al. *Meth. Enzymol.* 21: 470-480 (1981) and Angerer et al. in *Genetic Engineering: Principles and Methods* (Setlow and Hollander, eds.), vol. 7, pp. 43-65 (Plenum Press, New York 1985). See also U.S. Pat. Nos. 6,335,167; 6,197,501; 5,830,645; and 5,665,549; the disclosures of which are incorporated herein by reference.

The description also provides microarrays or microarray platforms designed by the methods described herein. The microarrays comprise a solid support and a plurality of surface bound probes, the surface bound probes having very similar thermodynamic properties as well as similar GC content. More specifically, a large portion of the probes utilized in the microarrays of the invention, have duplex melting temperatures ($T_m$) which are within a narrow temperature range compared to the $T_m$ range of probes for other microarray systems, such as arrays for gene expression.

In some embodiments, a nucleic acid array comprises at least one probe that is complementary to a sequence of a gene comprising a SNP, wherein the SNP is cut by a first restriction enzyme, but not by a second restriction enzyme. In other embodiments the array further comprises a probe that is complementary to a wild-type sequence corresponding to the sequence comprising the SNP site. In yet another embodiment, the array further comprises at least one probe that is complementary to a sequence of the gene comprising a second SNP site, wherein the second SNP is not cleaved by the first restriction enzyme, but is cleaved by a second restriction enzyme. In some embodiments, the array may comprise a probe comprising a base deletion in the sequence comprising a SNP or a generic base in the sequence comprising the SNP. In some embodiments, the probe sequence is selected to bind to a target sequence comprising a restriction enzyme cleavage sequence, wherein the probe sequence binds to the restriction enzyme cleavage sequence in the middle of the probe sequence. In some embodiments, each probe has a $T_m$ difference of about 0.5° C. to about 4° C. when compared to a perfectly matched probe.

The present systems, techniques, methods and computer readable media also provide for streamlined workflow, since researchers need only to prepare and process one microarray instead of two or more per sample, with fewer steps in processing and tracking required.

Further, greater reproducibility of results is provided for, since all data for an entire genome is generated from a single microarray, resulting in less variability in the data. When two or more microarrays associated with the same sample are processed separately, there are always questions of variability of the experimental conditions used to process each microarray.

Methods for Designing a Microarray Platform for Allelic Detection

The methods described herein are directed to designing microarray platforms for use in CGH applications, particularly for the detection of SNP sites in an allele or for detection of allele-specific copy number. A set of potentially informative SNP sites in a target region of interest, such as a human genome reference assembly, is determined. Two or more restriction enzymes are selected, and the set of SNP sites in the target region of interest that can be cut by a combination of the two or more enzymes is calculated.

Various restriction enzymes such as 4-, 5- or 6-base cutting enzymes, and combinations of such enzymes can be used with the methods described herein. Exemplary 4-base cutter enzymes of the methods comprise RsaI and AluI. After adjusting for multiple overlapping restriction sites or repeat masked regions, a reduced subset of SNP sits suitable for the "real estate" of a microarray platform can be determined, and the number of SNPs can be incorporated into the array platform. Such arrays can be used for CGH experiments to detect allele-specific copy number changes. The selection of the optimal subset of sites for use on the array is influenced by the informativity of the sites by any of the following factors: the frequencies of the SNPs in the population of interest, because minor alleles that occur frequently are more informative, the existence of SNPs with known phenotypes, or regions of the genome such as regions within genes of interest associated with particular diseases, or gene regulatory sequences.

The total number of SNP sites that can be cut by the combination of enzymes is then reduced by omitting multiple cleavage sites (about 0.6%), or sites that overlap with repeat masked regions of the genome. To eliminate repeat masked regions, the RepeatMasker software program is used, which eliminates regions of the genome containing repetitive sequences. The software uses a database of known sequences and algorithms to determine repetitive sequences in order to "mask" them in any sequence. The identified SNP sites that fall within the repeat mask criteria are omitted, thereby reducing the total number of SNP sites by about 49%.

After multiple restriction sites and repeat masked regions have been omitted, a reduced set of about 218,000 SNP sites is obtained. This reduced set of SNP sites can then be incorporated into the microarray platform design. With 244,000 features currently possible on an array, and at two probes per SNP, one for each allelic state, the reduced number of SNPs identified by the present methods could exceed the "real estate" currently available on the array. However, the methods can be optimized to accommodate a larger number of SNPs. For example, the methods can be optimized by using a larger number of enzymes to optimize the distribution of SNPs across the reference assembly. The methods can also be optimized by using enzymes with larger cleavage sites (i.e. more bases per cut site) to explore more of the genomic sequence per site. Using enzymes with larger cleavage sites reduces the total number of cleavage sites (relative to enzymes with smaller cleavage sites) but covers significantly more genomic space. Using enough enzymes with distinct cleavage sites in combination produces an ideal number of SNP sites for assay. More complex mixtures of enzymes would increase significantly the number of available SNP sites to be explored. For example, by using multicolor array systems (i.e. assays beyond 2-, 3- and 4-color), or by using platforms comprising arrays of arrays, the present methods can be substantially expanded, allowing for the analysis of allele-specific copy number changes.

In an assay to detect allele-specific copy number changes, a plurality of test samples are collected from subjects of patients for CGH analysis. In an aspect, each sample is split to provide at least two sub-samples. The sub-samples are digested and each sub-sample is labeled with a different fluorophore, such that each labeled sub-sample occurs in a different color channel of a two-color microarray system. One of the sub-samples is then treated with a restriction enzyme, while the other sub-sample is left untreated enzymatically, or cut with another enzyme for which there are no site-specific probes on the microarray. The sub-samples are hybridized to a microarray with a first probe corresponding to a wild-type sequence for a polymorphic SNP site, and a second probe corresponding to a mutant sequence for the same polymorphic SNP site. A subsequent CGH assay identifies the mutated SNP site, and can be used to determine allele-specific copy number changes.

In variations of these assay methods, an unpooled test sample with a set of known SNP states can be used as a reference sample. For each polymorphic SNP site, the state of the sample can then be identified on the basis of the ratio of the signal obtained from the reference sample and the signal obtained from the test sample. Multi-color labeling reactions involving more than two reporter (i.e. chromogenic or fluorophore) moieties can be used in place of hybridization reactions involving only two color reactions. In aspects, during digestion, one sample or sub-sample is digested, whereas the other sample or sub-sample is left undigested. Similarly, the two (or more) samples or sub-samples may be treated with different restriction enzymes such that a site cut by one enzyme in one sub-sample will remain uncut by a different enzyme in a different sub-sample. The assay may also be performed with probe variants, wherein the probe has a base deletion at a SNP site, or has a generic base at the SNP site. In this way, only a single probe is needed to detect both SNP states, with a somewhat reduced signal relative to the perfect match sequence. The variant probes can be then be hybridized to the microarray as in a standard CGH experiment.

Methods for designing a microarray platform are optimized using in silico parameters. That is, oligonucleotide probes contained on the microarray are designed according to one or more additional parameters that may be suitable for a given microarray application. In silico parameters used with the methods herein include, without limitation, length of the probes, melting temperature ($T_m$), non-homology with other regions of the genome, hybridization signal intensities, kinetic properties under hybridization conditions, etc. In silico parameters are described in more detail in U.S. Pat. No. 6,251,588, the disclosure of which is incorporated herein by reference.

Microarray platform design is performed using a computational analysis system with comprises a computer-readable medium with a program for determining and calculating SNP sites as in the methods described herein. The methods can be used to produce or fabricate microarrays comprising probes selected to take into account SNP sites and mutations thereof.

Arrays

The present description also provides nucleic acid microarrays produced using the subject methods, as described herein. The subject arrays include at least two distinct nucleic acids that differ by monomeric sequence immobilized on, e.g., covalently on, different and known locations on the substrate surface. In certain embodiments, each distinct nucleic acid sequence of the array is typically present as a composition of multiple copies of the polymer on the substrate surface, e.g., as a spot on the surface of the substrate. The number of distinct nucleic acid sequences, and hence spots or similar structures, present on the array may vary, but is generally at least 2, usually at least 5 and more usually at least 10, where the number of different spots on the array may be as a high as 100, 1000, 10,000, 100,000, 1,000,000 or higher, depending on the intended use of the array. The spots of distinct polymers present on the array surface are generally present as a pattern, where the pattern may be in the form of organized rows and columns of spots, e.g., a grid of spots, across the substrate surface, a series of curvilinear rows across the substrate surface, e.g., a series of concentric circles or semicircles of spots, and the like. The density of spots present on the array surface may vary, but will generally be at least about 10 and usually at least about 100 spots/cm$^2$, where the density may be as high as $10^6$ or higher. In other embodiments, the polymeric sequences are not arranged in the form of distinct spots, but may be positioned on the surface such that there is substantially no space separating one polymer sequence/feature from another. An exemplary array is described in U.S. Patent Publication No. 20050095596, which is incorporated herein by reference.

Arrays can be fabricated using drop deposition from pulse-jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. These references are incorporated herein by reference. Other drop deposition methods can be used for fabrication, as previously described herein.

A feature of the subject arrays is that they include one or more, usually a plurality of, oligonucleotide probes predicted by the statistical methods described herein. The oligonucleotide probes selected according to the subject methods are suitable for use in a plurality of different gene expression or genomic microarray applications. The statistical regression method evaluates probe performance, without using any assumptions about the functional relationship between the oligonucleotide sequence and the predictive parameters. Oligonucleotide probes that "cluster" (i.e. consistently produce the same response) will perform substantially similarly under a plurality of different experimental conditions.

The arrays as described herein can be used in a variety of different microarray applications, including gene expression experiments and genomic analysis. In using an array, the array will typically be exposed to a sample (for example, a fluorescently labeled analyte, such as a sample containing genomic DNA) and the array then read. Reading of the array may be accomplished by illuminating the array and reading the location and intensity of resulting fluorescence at each feature of the array to detect any binding complexes on the surface of the array. For example, a scanner may be used for this purpose that is similar to the AGILENT MICROARRAY SCANNER available from Agilent Technologies, Palo Alto, Calif. Other suitable apparatus and methods are described in U.S. patent application Ser. No. 09/846,125 "Reading Multi-Featured Arrays" by Dorsel et al.; and Ser. No. 09/430,214 "Interrogating Multi-Featured Arrays" by Dorsel et al. As previously mentioned, these references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample or an organism from which a sample was obtained exhibits a particular condition). The results of the reading (processed or not) may be forwarded (such as by communication) to a remote location if desired, and received there for further use (such as further processing).

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

Systems

The methods described herein are carried out in part with the aid of a computer-based system, driven by software specific to the methods. A "computer-based system" refers to the hardware, software, and data storage used to analyze the information of the present disclosure. Typical hardware of the computer-based systems of the present disclosure comprises a central processing unit (CPU), input, output, and data storage. A skilled artisan can readily appreciate that any one of the currently available computer-based system are suitable for use in the present disclosure. The data storage means may comprise any manufacture comprising a recording of the present information as described above, or a memory access means that can access such a manufacture. In certain instances a computer-based system may include one or more wireless devices.

To "record" data, programming or other information on a computer-readable medium refers to a process for storing information on a recordable storage medium, using any such methods as known in the art. Examples include magnetic media such as hard drives, tapes, disks, and the like. Optical media can include CDs, DVDs, and the like. Any convenient data storage structure may be chosen, based on the means used to access the stored information. A variety of data processor programs and the formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In aspects, the methods described herein are performed using computer-readable media containing programming stored thereon implementing the subject methods. The computer-readable media may be, for example, in the form of a computer disk or CD, a floppy disk, a magnetic "hard card", a server, or any other computer-readable media capable of containing data or the like, stored electronically, magnetically, optically or by other means. Accordingly, stored programming embodying steps for carrying out the subject methods may be transferred to a computer such as a personal computer (PC), (i.e. accessible by a researcher or the like), by physical transfer of a CD, floppy disk, or like medium, or may be transferred using a computer network, server, or any other interface connection, e.g., the Internet.

In an embodiment, the system described herein may include a single computer or the like with a stored algorithm capable of evaluating probe performance, as described herein, i.e. a computational analysis system that calculates the number of SNP sites, and the number of cuts that a restriction enzyme will produce in a particular sequence. In certain embodiments, the system is further characterized in that it provides a user interface, where the user interface presents to a user the option of selecting among one or more different, or multiple different inputs. For example, in the systems described herein, the user has the option of selecting various predictive parameters, such as composition factors, thermodynamic factors, kinetic factors, and mathematical combinations of such factors, as well as analogous parameters for the intended genomic targets. Computational systems that may be readily modified to become systems of the subject invention include those described in U.S. Pat. No. 6,251,588, the disclosure of which is incorporated herein by reference.

The various embodiments described above are provided by way of illustration only and should not be construed to limit the invention. Those skilled in the art will readily recognize various modifications and changes that may be made to the present methods without following the example embodiments and applications illustrated and described herein, and without departing from the true spirit and scope of the claims attached hereto.

Example 1

A set of potentially informative SNP sites in a target region of interest, such as a human genome reference assembly, was determined. The SNP sites that are cleaved by RsaI or AluI were identified by searching the sequences for restriction site cleavage sequences. After adjusting for multiple overlapping restriction sites or repeat masked regions, a reduced subset of SNP sites that are cleaved either by enzymes RsaI or AluI was obtained. To eliminate repeat masked regions, the RepeatMasker software program was used, which eliminates regions of the genome containing repetitive sequences. The software uses a database of known sequences and algorithms to determine repetitive sequences in order to "mask" them in any sequence. The identified SNP sites that fall within the repeat mask criteria are omitted, thereby reducing the total number of SNP sites by about 49%.

After multiple restriction sites and repeat masked regions have been omitted, a reduced set of about 218,000 SNP sites was obtained. This reduced set of SNP sites can then be incorporated into the microarray platform design. With 244,000 features currently possible on an array, and at two probes per SNP, one for each allelic state, the reduced number of SNPs identified by the present methods could exceed the "real estate" currently available on a single array. If necessary, additional arrays can be utilized and the methods can be optimized to accommodate a larger number of SNPs.

In an assay to detect allele-specific copy number, human genomic DNA samples were collected from individuals and pooled. The pooled sample was predigested with the restriction enzyme RsaI to generate fragments of genomic DNA. The sample was then split to provide at least two sub-samples. One of the sub-samples was digested with AluI and each sub-sample was labeled with a different fluorophore, such that each labeled sub-sample occurs in a different color channel of a two-color microarray system. The sub-samples were hybridized to a microarray containing a first probe comprising a sequence that binds to a wild-type sequence for a SNP site, and a second probe comprising a sequence that binds to a sequence comprising the SNP site. The array included a probe that detected an ErbB4 gene and an allele of the ErbB4. The allele contained a SNP site that was cleaved by the AluI enzyme.

An unpooled reference sample with a known allelic copy number was used as a reference sample for the ErbB4 allele. The allelic copy number of the allele in the sample was identified on the basis of the ratio of the signal obtained from the reference sample and the signal obtained from the undigested subsample.

As shown in FIG. 2, at least one site detected by a single probe showed differential copy number measurements between samples in the ErbB4 gene. Different samples from multiple individuals show a distribution for a given probe, with three distinct clusters of LogRatio values. One cluster indicates that the samples were cut homozygously relative to the reference that there were two copies of the same allele present in the sample). Another cluster demonstrates that only a single allele corresponding to one of the two copies of chromosome-2 is cut by the enzyme (i.e. heterozygously; a single copy of the allele present in the sample), and a third set indicates a situation where the allele that is present on both copies of chromosome 2 is not cleaved.

The invention claimed is:

1. A method for sample analysis, comprising:
   a) contacting a first DNA sample with a first restriction enzyme to provide a digested sample, wherein:
      i) said DNA sample may comprise a target sequence comprising a SNP site; and
      ii) said first restriction enzyme cleaves said target sequence at a cleavage site only if a first allele of a SNP is present at said SNP site;
   b) hybridizing said digested sample to a surface-bound polynucleotide comprising a probe sequence that hybridizes to said target sequence wherein:
      i. the surface-bound polynucleotide is up to 200 nucleotides in length,
      ii. the probe sequence comprises said cleavage site, and
      iii. the probe sequence is designed such that cleavage of the target sequence at said cleavage site by said first restriction enzyme results in less hybridization of the digested sample relative to a sample in which the target sequence is undigested by the first restriction enzyme;
   c) comparing the hybridization signal between the digested sample and the probe sequence to a reference signal, and
   d) determining whether the first allele of the SNP is present in the DNA sample, wherein the hybridization signal of the digested sample to the probe sequence as compared to the reference signal indicates whether the first allele of said SNP is present in the DNA sample.

2. The method of claim 1, wherein said reference signal is the hybridization signal between a reference sample and the probe sequence, wherein the reference sample comprises one or more known alleles of the SNP at said SNP site and has been contacted with said first restriction enzyme.

3. The method of claim 1, wherein said reference signal is the hybridization signal between a reference sample and the probe sequence, wherein the reference sample is a second portion of said first DNA sample that has not been contacted with said first restriction enzyme.

4. The method of claim 2, wherein said reference sample comprises a plurality of DNA samples from different subjects.

5. The method of claim 1, wherein said surface-bound polynucleotide is from 30 to 60 nucleotides in length.

6. The method of claim 5, wherein, in said probe sequence, the nucleotide immediately 5' of said cleavage site is located within at least 10 nucleotides from the center of the probe sequence.

7. The method of claim 1, wherein said probe sequence is complementary to a second allele of said SNP.

8. The method of claim 1, wherein the probe sequence comprises a base deletion at a position that corresponds to the SNP site.

9. The method of claim 1, wherein the probe sequence has a generic base at the SNP site.

10. The method of claim 1, further comprising determining whether said DNA sample is homozygous or heterozygous for said first allele.

11. The method of claim 1, further comprising determining the copy number of said target sequence.

12. The method of claim 1, wherein the first DNA sample is fragmented genomic DNA.

13. The method of claim 1, wherein the first restriction enzyme is a four base cutter.

14. The method of claim 1, wherein the first restriction enzyme is a five base cutter.

15. The method of claim 1, wherein the first restriction enzyme is a six base cutter.

16. The method of claim 1, wherein the first restriction enzyme is RsaI.

17. The method of claim 1, wherein the first restriction enzyme is AluI.

18. The method of claim 2, wherein said digested sample and the reference sample are co-hybridized to the same array.

19. The method of claim 1, wherein the first DNA sample is a cDNA sample.

20. The method of claim 1, wherein the surface-bound polynucleotide is part of an array.

21. The method of claim 1, wherein said first DNA sample is not a PCR product.

* * * * *